United States Patent [19]

Patel

[11] Patent Number: 4,841,090

[45] Date of Patent: Jun. 20, 1989

[54] TREATMENT OF FIBROUS SUBSTRATES, SUCH AS CARPET, WITH FLUOROCHEMICAL

[75] Inventor: Kalyanji U. Patel, Maplewood, Minn.

[73] Assignee: Minnesota Mining and Manufacturing Company, St. Paul, Minn.

[21] Appl. No.: 102,259

[22] Filed: Sep. 29, 1987

Related U.S. Application Data

[63] Continuation of Ser. No. 805,589, Dec. 9, 1985, abandoned, which is a continuation of Ser. No. 387,444, Jun. 11, 1982, abandoned.

[51] Int. Cl.$^4$ .................... C07C 121/66; C07C 121/75

[52] U.S. Cl. ........................................ 558/437; 8/602; 8/603; 428/288; 548/519; 549/552; 558/430; 560/25; 560/118; 560/150; 560/169; 562/579

[58] Field of Search ........................ 558/437, 430, 451

[56] References Cited

U.S. PATENT DOCUMENTS

| | | | |
|---|---|---|---|
| 3,329,661 | 7/1967 | Smith et al. | 260/79.3 |
| 3,458,571 | 7/1969 | Tokoli | 260/556 |
| 3,564,043 | 2/1971 | Eiseman et al. | 260/465 X |
| 3,574,791 | 4/1971 | Sherman et al. | 260/884 |
| 3,622,590 | 11/1971 | Gresham | 260/297 R |
| 3,728,151 | 4/1973 | Sherman et al. | 117/138.8 |
| 3,916,053 | 10/1975 | Sherman et al. | 428/96 |
| 4,013,627 | 3/1977 | Temple | 526/245 |
| 4,144,367 | 3/1979 | Landucci | 428/96 |
| 4,165,338 | 8/1979 | Katsushima et al. | 260/584 R |
| 4,215,205 | 7/1980 | Landucci | 525/331 |
| 4,264,484 | 4/1981 | Patel | 260/29.6 |
| 4,356,273 | 10/1982 | Soch | 521/114 |
| 4,525,305 | 6/1985 | Patel | 562/439 X |

FOREIGN PATENT DOCUMENTS

| | | |
|---|---|---|
| 1928985 | 1/1970 | Fed. Rep. of Germany . |
| 2016019 | 4/1970 | Fed. Rep. of Germany . |
| 1793486 | 12/1971 | Fed. Rep. of Germany . |
| 2196416 | 3/1974 | France . |
| 2075514 | 5/1980 | United Kingdom . |

OTHER PUBLICATIONS

Organic Functional Group Preparations; Sandler & Karo; Academic Press; N.Y. & London (1968), pp. 334–335.

AHIBA; Turbomat TM 6B, Bulletin A–102–B–D–E–I, (49 pp & 22 unnumbered pages) 79 pages (undated).

Launder-Ometer, Model LEF, Bull. No. 1295B of the Atlas Electric Devices, Co., (9/73), 4 pp. bulletin.

Lovelace et al.; "Aliphatic Fluorine Compounds", (1958); pp. 296,297,299, Reinhold Pub. Co., N.Y.

Braces, J. Org. Chem., 36, No. 21, (1971), pp. 3187–3191.

Banks, "Fluorocarbons and Their Derivatives", (1964), pp. 48–53, Oldbourne Press, London.

Fieser et al., "Organic Chemistry", (1956), pp. 4–5, Reinhold Pub. Corp. N.Y.

Richardson et al., Brief College Chemistry, date unknown, pp. 2,3,208,209; Holt and Co., N.Y.

March, Advanced Organic Chemistry, (1968); pp. 331–332, McGraw-Hill Book Co., N.Y.

Kirk-Othmer, Encyclopedia of Chemical Technology, vol. 19, 3rd ed., (1982), pp. 521–531.

Cotton et al.; Advanced Inorganic Chemistry, (1962), pp. 168–183.

Concise Chemical and Technical Dictionary (1974), edited by Bennett, pp. 13, 35 and 618.

Noller, Chemistry of Organic Compounds, 2nd ed., (1957), pp. 288, 745, 788.

Pine et al., Organic Chemistry, 4th ed. (1980), pp. 416, 417, 419.

Hackh's Chemical Dictionary, Grand, 4th ed. pp. 62, 642.

*Primary Examiner*—Joseph Paul Brust
*Attorney, Agent, or Firm*—D. M. Sell; C. Truesdale

[57] ABSTRACT

Fluorochemical amine salt compounds containing one or more fluoroaliphatic radicals and one or more salt-forming amino groups which have cyanoalkyl groups as N-substituents groups, such compounds being useful as treating agents for fibrous substrates, such as textiles, e.g., carpet, to modify surface properties thereof, viz., to impart oil and water repellency to the surface of said substrates.

6 Claims, No Drawings

TREATMENT OF FIBROUS SUBSTRATES, SUCH AS CARPET, WITH FLUOROCHEMICAL

This is a continuation of application Ser. No. 805,589 filed Dec. 9, 1985, now abandoned, which is a continuation of application Ser. No. 387,444 filed June 11, 1982 now abandoned.

This invention relates to the treatment of fibrous substrates, such as textiles, paper, and leather, and particularly to the treatment of carpet, with fluorochemical, and to the resulting treated substrates. In another aspect, it relates to fluorochemicals, and their preparation, which are useful in such treatment.

In the industrial production of textiles, such as carpet and apparel, and such other fibrous, porous substrates as paper and leather, it is common to treat the surfaces of such substrates with fluorochemicals containing fluoroaliphatic radicals (often designated by the symbol "$R_f$") to modify the surface properties of such substrates. The $R_f$ radicals have extremely low free-surface energy, high chemical stability, and are hydrophobic and oleophobic, and thus such chemicals impart oil and water repellency to the treated surface. Fluorochemicals of this type and their application of fibrous substrates are described in various prior art publications, e.g., U. S. Pat. Nos. 3,329,661 (Smith et al), 3,458,571 (Tokoli), 3,574,791 (Sherman et al), 3,728,151 (Sherman et al), 3,916,053 (Sherman et al), 4,144,367 (Landucci), 4,165,338 (Katsushima et al), 4,215,205 (Landucci), 4,013,627 (Temple), and 4,264,484 (Patel) and U.K. patent application No. 2,075,514 A.

Although some fluorochemicals are useful in many applications and many are commercial products, some are relatively expensive to prepare and apply and others do not impart the required properties to the degrees desired.

Briefly, this invention provides in one aspect non-polymeric fluorochemicals, namely fluorochemical amine compounds, containing one or more fluoroaliphatic radicals ($R_f$) and one or more salt-forming amino groups which can have as N-substituents groups containing electron-withdrawing moieties, e.g. cyano, carbonyl, alkoxycarbonyl, carboxamido, and phenyl, and salts of such amine compounds, such fluorochemicals being useful as treating agents, e.g. in the form of an aqueous dispersion of said salt, for fibrous substrates, such as textiles, e.g. carpet such as nylon carpet, to modify surface properties thereof, e.g. to impart oil and water repellency to the surface of said substrates. The treating agents of this invention are thus non-ionic compounds, i.e., free amine compounds, or salts of free amine compounds.

A class of such fluorochemical compounds can be represented by the general formula

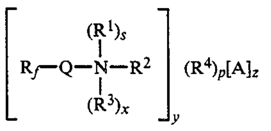

where $R_f$ is a fluoroaliphatic radical,

Q is an organic linking moiety,

N is a salt-forming amino nitrogen atom, $R^1$ is a hydrogen or an alkyl group, $R^2$ is a monovalent group selected from the class of $R_fQ$—, alkyl and aryl groups, and combinations of such groups, e.g. alkaryl, which groups can contain a hetero atom, e.g. —O— or —S—, RCONH— (where R is alkyl or aryl), and

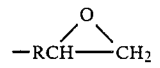

(where R is alkylene), or $R^2$ is a divalent group selected from the class of alkylene and arylene groups, combinations thereof, and —RCONH— (where R is alkylene or arylene), $R^3$ is hydrogen, an alkyl group which preferably is substituted with one or more polar moieties such as —OH, —COO—, $>C{=}CH_2$, or $R^3$ can be $R_f$—Q— or $—CH_2CH_2E$ where E is an electron-withdrawing moiety such as

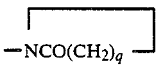

(where q is 3 to 5), $—CON(R)_2$, —CN, —COOR, $—C_6H_4R$, or $—SO_2R'$, where R is hydrogen or alkyl, and R' is alkyl or aryl, $R^4$ is an alkylene or arylene group, A is an anion derived from a protonic acid or an alkylating agent, s is 0 or 1, x is 0 or 1, y is 1 to 4, preferably 1 or 2, p is 0 or 1, and z is 0 to 4, preferably 0 to 2, with the provisos that (1) when y is 1, then p is 0 and z is 0 or 1, (2) when y is 2, then $R^2$ is said divalent group, and (3) the sum of s and x is at least 1.

In the above formula, the alkyl groups in $R^1$, $R^3$, and R can have 1 to 6 carbon atoms, the alkyl in $R^2$ can have 1 to 18 carbon atoms, the alkylene groups of $R^2$ and $R^4$ can have 1 to 12 carbon atoms, and the aryl and arylene groups can have 6 to 12 carbon atoms.

A preferred subclass of the fluorochemicals of formula I is:

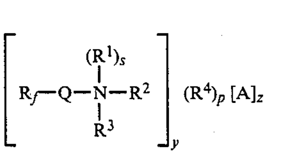

II where $R_f$, Q, $R^1$, $R^4$, and A are as defined for formula I, $R^2$ is alkyl or alkylene as defined for formula I, $R^3$ is $-CH_2CH_2E$, where E is as defined for formula I, s is 0 or 1, y is 1 or 2, p is 0 or 1, and z is 0 to 2, with the provisos that when y is 1, then p is 0 and z is 0 or 1, and when y is 2, then $R^2$ is a said divalent group.

The fluoroaliphatic radical, $R_f$, is a fluorniated, stable, inert, non-polar, preferably saturated, monovalent moiety which is both oleophobic and hydrophobic. It can be straight chain, branched chain, and, if sufficiently large, cyclic, or combinations thereof, such as alkylcycloaliphatic radicals. The skeletal chain can include catenary oxygen and/or trivalent nitrogen hetero atoms bonded only to carbon atoms, such hetero atoms providing stable linkages between fluorocarbon groups and not interferring with the inert character of the $R_r$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. Generally, $R_f$ will have 3 to 20 carbon atoms, preferably 6 to about 12, and will contain 40–78 weight percent, preferably 50–78 weight percent, of fluorine. The terminal portion of the $R_f$ group has preferably at least three fully fluorinated carbon atoms, e.g. $CF_3CF_2CF_2$—, and the preferred compounds are those in which the $R_f$ group is fully or substantially completely fluorinated, as in the case where $R_f$ is perfluoroalkyl, $C_nF_{2n+1}$.

Generally, the fluorochemical compound will contain about 20 to 65 weight percent, preferably about 30 to 55 weight percent, of carbon-bonded fluorine. If the fluorine content is less than about 20 weight percent, impractically large amounts of the fluorochemical compound will generally be required, while fluorine contents greater than about 65 weight percent are unnecessary to achieve the uneconomical use of fluorine.

The function of the linkage or bridge Q is to bond the fluoroaliphatic radical, $R_f$, to the amine moiety of the compound. Q can comprise one or a combination of groups such as polyvalent aliphatic, e.g., $—CH_2—$, $—CH_2CH_2—$, and $—CH_2CH(CH_2—)_2$, polyvalent aromatic, oxy, thio, carbonyl, sulfone, sulfoxy, $—N(C_2H_5)—$, sulfonamido, carbonamido, sulfonamidoalkylene, carbonamidoalkylene, hydroxymethylene, carbonyloxy, urethane, e.g., $—CH_2CH_2OCONH—$, and urea, e.g., —NHCONH—. The linkage Q for a specific compound useful in this invention will be dictated by the ease of preparation of such a compound and the availability of necessary precursors thereof. From the above description of Q, it is apparent that this linkage can have a wide variety of structures. Since N is a nitrogen atom of a salt-forming amino group, it follows that the moiety of Q which is bonded to N cannot be an electrophilic moiety, such as carbonyl, sulfonyl, etc., which would preclude said nitrogen atom from being that of a salt-forming amino group. However large Q is, the fluorine content (the locus of which is $R_f$) of the compound is in the aforementioned limits.

The above-described fluorochemical compounds can be prepared by reacting fluoroaliphatic radical-containing intermediates (that is, $R_f$ intermediates, which generally are commercially made by electro-chemical fluorination of organic acids or halides thereof or by telomerization of tetrafluoroethylene, followed by known reactions to form said intermediates) and selected organic reagents. Such reactions are carried out neat or in the presence of polar non-reactive solvents, such as ethyl acetate, at moderate temperatures, such as 50° to 130° C.

Suitable $R_f$ precursors for this purpose include the following representative compounds

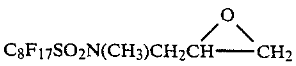

-continued

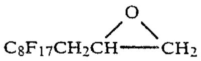

$C_8F_{17}SO_2N(CH_3)C_2H_4OCOCH=CH_2$
$C_8F_{17}C_2H_4OCOCH=CH_2$
$C_8F_{17}SO_2N(C_2H_5)C_2H_4OH$
$C_8F_{17}SO_2NHC_2H_4NH_2$

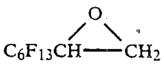

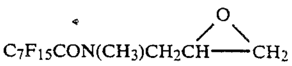

$C_7F_{15}CON(CH_3)C_2H_4OCOCH=CH_2$
$C_8F_{17}C_2H_4SC_2H_4OCOCH=CH_2$
$(CF_3)_2CF(CF_2)_8C_2H_4SCOCH=CH_2$
$C_8F_{17}CH_2NCO$

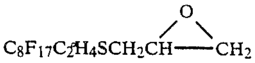

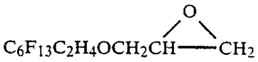

The organic reagents which are reacted with the $R_f$ precursors to prepare the fluorochemical treating agents of this invention include the following representative amines $H_2N(CH_2)_6NH_2$

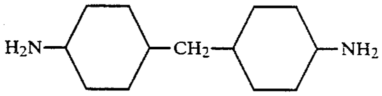

$H_2NCH_2C_6H_4CH_2NH_2$
$HOCH_2CH_2N(CH_3)CH_2CH_2OH$
$C_{18}H_{37}N(CH_3)CH_2CH_2OH$
$C_{17}H_{35}CONHC_3H_6NH_2$
$C_8H_{17}SO_2NHC_2H_4NH_2$
$H_2NNHCO(CH_2)_8CONHNH_2$.
$C_7H_{15}CONHNH_2$
$H_2NCH_2CH_2NHCH_2CH_2NH_2$ the following representative electrophilic olefins $CH_2=CHCN$
$CH_2=CHCOOC_2H_5$
$CH_2=CHCOOC_2H_4OC_2H_4CN$
$CH_2=CHCONH_2$
$CH_2=CHCOC_2H_4OH$

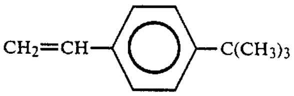

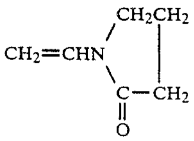

$CH_2=CHSO_2CH=CH_2$
$C_4H_9CON(CH_3)CH=CH_2$

-continued

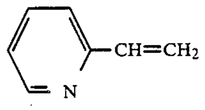

and the following representative polyisocyanates

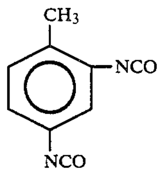

$OCN(CH_2)_6NCO$

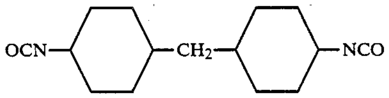

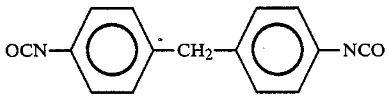

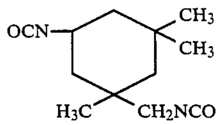

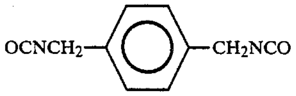

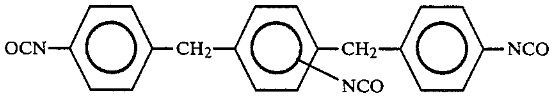

and the following representative aliphatic and aromatic epoxy compounds

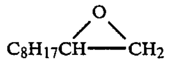

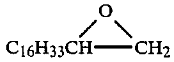

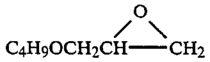

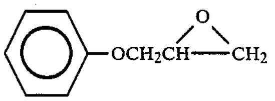

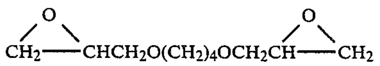

-continued

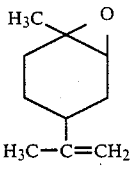

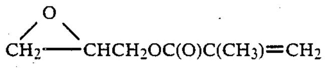

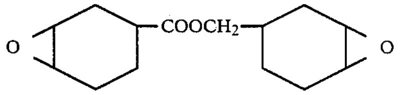

The fluorochemical amine compounds used in this invention generally can be prepared by reacting the fluoroaliphatic precursor, amine, and electrophilic olefin reactants together in appropriate molar ratios. Alternatively, such compounds can be prepared by reacting the amine and olefin together to form an adduct and then reacting the latter with the fluoroaliphatic precursor, or such compounds can be prepared by reacting the fluoroaliphatic radical precursor with the amine and then reacting the resulting adduct with the olefin. The water dispersible cationic derivatives or salts of the fluorochemical amine product can be prepared by neutralizing the latter with an acid (preferably a carboxylic acid, e.g. glycolic acid) to form a salt or by reaction with an alkylating agent (such as an alkyl halide or sulfate) to form a quaternary salt. These types of reactions are generally known (see, for example, the description of a Michael reaction in "Organic Functional Group Preparations" by S. R. Sandler and W. Karo, Academic Press, N.Y. 1968, p. 334).

Representative reaction schemes for the preparation of the fluorochemical amine compounds of this invention are as follows:

Scheme I

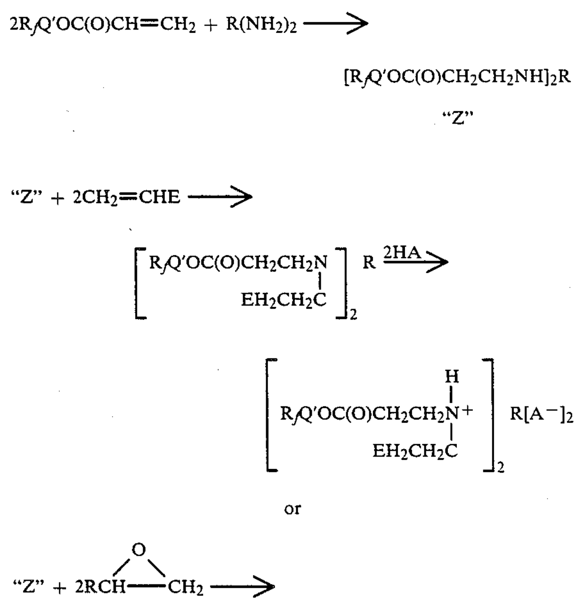

-continued

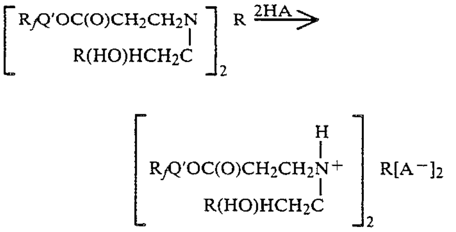

Scheme II

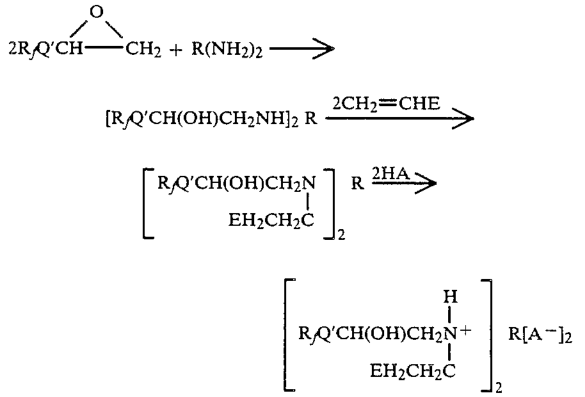

Scheme III

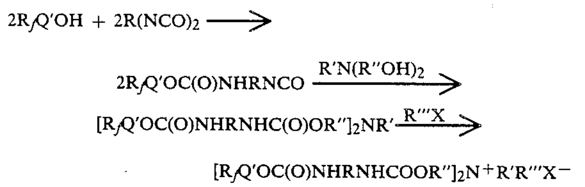

In general, the fibrous substrates are treated by contacting the surface thereof with the fluorochemical compounds of this invention. The particular mode of application of the fluorochemical compound will depend upon its particular nature as well as that of the particular substrate. In the case of the free amine fluorochemical, a solution of it in a solvent such as ethyl acetate or acetone can be applied, or the free amine can be emulsified in water with an added emulsifier and the emulsion applied. In the case of the fluorochemical salt, an aqueous dispersion (or emulsion) can be applied. Generally the concentration of the fluorochemical (free amine or salt) in such media will vary, as described below.

Broadly, the fibrous, substrates which can be treated in accordance with this invention are textiles, paper, paperboard, leather, and the like. The textiles include those made from natural fibers, such as cotton and wool, and those made from sythetic fibers, such as nylon, acetate, rayon, acrylic, and polyester fibers. The fibers (or yarn) can be treated as such or in an aggregated form, e.g. skein or roving, with the fluorochemical compound, or the fabricated textile, e.g., articles such as carpet and woven fabrics, can be treated with the fluorochemical compound. The treatment can be carried out by applying the fluorochemicals by known techniques customarily used in applying fluorochemicals to fibrous substrates. For example, the treatment can be by immersing the fibrous substrates in a bath containing the fluorochemical, padding the substrate or spraying the same with the fluorochemical, or by foam, kiss-roll, or metering applications, e.g. spin finishing, and then drying the treated substrates. If desired, the fluorochemical can be co-applied with adjuvants, e.g. antistatic agents or neat oil (fiber lubricant).

A particularly effective method for treating textiles, e.g. carpet, with the fluorochemical compound is to carry out the treatment in conjunction with the conventional dyeing of the textiles (see, for example, the series of dyeing primer articles appearing in "Textile Chemist and Colorist," Vol. 12, Jan.-Dec., 1980). The fluorochemical can be included in the carpet dyebath, in a scour rinse prior to dyeing, or in a water rinse after dyeing. By carrying out the fluorochemical treatment in conjunction with the dyeing of the carpet, economies in manufacturing oil and water repellent carpet are realized. Where the treatment of carpet is carried out in conjunction with its dyeing, e.g. beck dyeing, by adding the fluorochemical to the dyebath, the fluorochemical preferably is in the form of its salt, the compound in this form being self-emulsifiable and substantially completely exhausted from the dyebath onto the carpet fibers.

The dyebath can contain the usual adjuvants, such as buffering agents, leveling agents, pH adjusting chemicals, defoamers, softeners, sequestering agents, lubricants, etc., as well as the dyes, so long as they are compatible with the fluorochemical, which can be determined by simple laboratory screening tests. Non-ionic leveling agents are preferred for compatibility with the fluorochemical. Generally, acid, disperse, and basic (or cationic) dyes will be compatible with the fluorochemical salts of this invention.

In general, the fluorochemicals of this invention are applied at 50° to 130° C., preferably 70° to 100° C., for 10 to 60 minutes, as a solution or dispersion, e.g., in the aqueous dyebath, the concentration of the fluorochemical varying and being dependent on the mode of application. For application dependent on substantial exhaustion of the fluorochemical from the treating medium, the concentration will generally be 0.01 to 0.001 weight percent. For applications not involving exhaustion, e.g., padding, spraying, etc., higher concentrations will be needed. The amount of fluorochemical deposited on the treated substrate irrespective of the particular mode of application will be, functionally speaking, sufficient to impart the desired degree of oil and water repellency, and generally this amount will be 0.02 to 3, preferably 0.06 to 0.16, weight percent, or, expressed in terms of fluorine content, 0.01 to 1.5, preferably 0.03 to 0.08, weight percent fluorine.

Following application of the fluorochemical, the treated substrate will generally be dried by heating the substrate to remove volatile material, usually and primarily water. Surprisingly, in carrying out this drying, the temperature necessary to obtain the desired degree of oil and water repellency for many of the fluorochemicals of this invention will be relatively lower than that usually required in conventional industry practice. For example, such properties can be achieved by drying treated carpet at 70° C. in accordance with this invention, whereas a drying (curing) temperature of 100°–130° C. is common practice in treating carpet with fluorochemical.

Objects and advantages of this invention are illustrated in the following examples, the first series of examples describing the preparation of various fluorochemical compounds of this invention, the second series of examples describing their evaluation in the treatment of carpet during the dyeing thereof, and the balance of the examples describing the use of the fluorochemicals of this invention in the treatment of various other substrates.

EXAMPLES 1

In a 3-neck, 250 ml borosilicate glass flask, fitted with condenser, thermometer, stirrer, and electric heating mantle, were placed 58.3 g (0.1 mole) of N-methyl-N-(1,2 epoxypropyl)perfluorooctanesulfonamide, 5.8 g (0.05 mole) hexamethylene diamine, and 5.3 g (0.1 mole) of acrylonitrile. The resulting reaction mixture was heated to 80° C. and stirred for about four hours, the resulting viscous product solidifying on cooling the reaction mixture to room temperature. This product, a fluorochemical amine adduct, having the formula

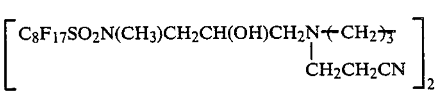

1A was mixed with 12 g. of 80 percent aqueous (0.1 mole) glycolic acid. The resulting mixture was heated to 80° C., mixed vigorously with 280 ml deionized water to yield a stable 20 percent aqueous dispersion of cationic fluorochemical amine salt compound having the formula:

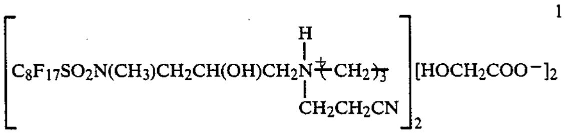

1

EXAMPLES 2-5

Other salts of the above-described adduct 1A of Example 1 were prepared in a similar manner except that the glycolic acid was replaced with various other acids, or with diethyl sulfate alkylating agent. Stable aqueous dispersions of the resulting cationic fluorochemicals were prepared as described above. The formulas for these salts are:

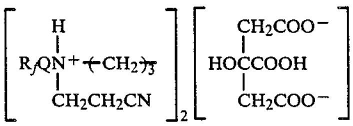

2

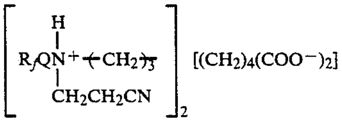

3

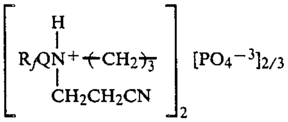

4

-continued

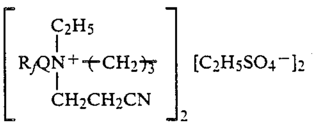

5 where $R_f$ is $C_8F_{17}$— and Q is —$SO_2N(CH_3)CH_2CH(OH)CH_2$—.

EXAMPLES 6-10

Five other fluorochemical amine salts were prepared in a manner similar to that described in Example 1 except that the electrophilic olefin used was N-vinylpyrrolidone, p-(t-butyl)styrene, acrylamide, or ethyl acrylate. The formulas for these salts are:

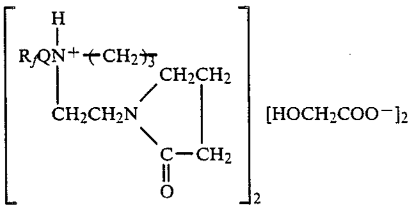

6

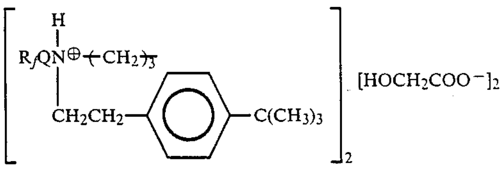

7

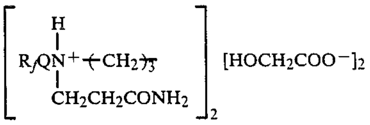

8

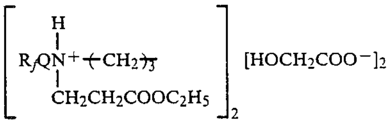

9

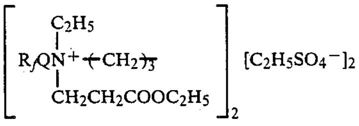

10 where $R_f$ and Q are the same as in formulas 2-5.

EXAMPLE 11

Another fluorochemical amine salt compound of the formula

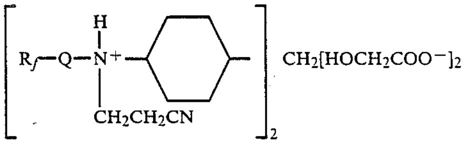

11 where $R_f$ and Q are as in formulas 2–5, was prepared in the manner similar to that of Example 1 except that in place of hexamethylene diamine there was used methylenebis(cyclohexylamine).

EXAMPLE 12

Another fluorochemical amine salt compound of the formula

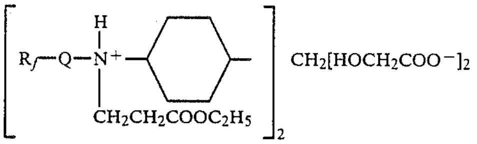
12 where $R_f$ and Q are as in formulas 2-5 was prepared in a manner similar to Example 1 except that the amine used was methylenebis(cyclohexylamine) and the olefin used was ethyl acrylate.

EXAMPLE 13

Another fluorochemical amine salt compound was prepared in a manner similar to Example 1 by reacting 1,2-epoxy-3-perfluorooctyl-1,1,2,3,3-pentahydropropane (in ethyl acetate solvent) with hexamethylene diamine, and then reacting the resulting adduct with acrylonitrile.

The resulting product of the formula

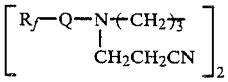
13A was neutralized with glycolic acid to form a salt of the formula

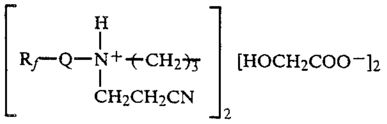
13 where $R_f$ is $C_8F_{17}$— and Q is —$CH_2CH(OH)CH_2$.

EXAMPLES 14–16

Three other fluorochemical amine salt compounds were prepared by reacting hexamethylene diamine or methylenebis(cyclohexylamine) with N-methylperfluorooctanesulfoamidoethyl acrylate, then reacting the resulting adducts with acrylonitrile, and then forming the salt, following the procedure of Example 1. The formulas for these three salts are

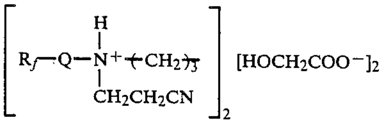
14

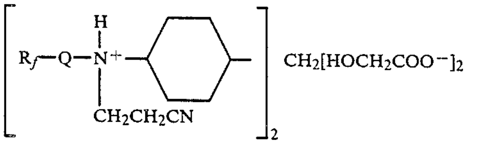
15

-continued

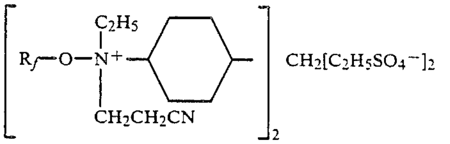
16 where $R_f$ is $C_8F_{17}$— and Q is —$SO_2N(CH_3)C_2H_4OCOC_2H_4$—.

EXAMPLE 17

Another fluorochemical amine salt was prepared in a manner similar to Example 1 by reacting N-methylperfluorooctanesulfonamidoethyl acrylate with perfluorooctanesulfonamidoethyl amine in ethyl acetate solvent, then reacting the resulting adduct with acrylonitrile, the resulting product then being neutralized with glycolic acid to form the corresponding salt, the formula of which is

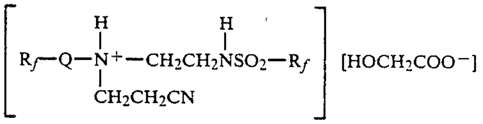
17 where $R_f$ and Q are as in formula 14.

EXAMPLE 18

Another fluorochemical amine salt was prepared, following the procedure of Example 1, by reacting N-methylperfluorooctanesulfonamidoethyl acrylate, hexamethylene diamine and N-methyl-N-(1,2-epoxypropyl)perfluorooctanesulfonamide and neutralizing the resulting amino adduct with glycolic acid to form the corresponding salt, the formula of which is

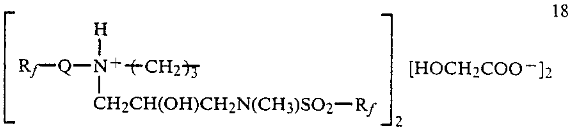
18 where $R_f$ and Q are as in formula 14.

EXAMPLE 19

In a flask such as that used in Example 1 were placed 110.8 g (0.2 mole) N-ethylperfluorooctanesulfonamidoethyl alcohol, 34.8 g (0.2 mole) 2,4-toluenediisocyanate, and 50 g ethyl acetate solvent. The mixture was stirred while heating it slowly to reflux (85°-90° C.) and maintained at reflux for about 1.5 hours. The reaction mixture was then cooled to 70° C. and 3 drops of dibutyl tin dilaurate urethane catalyst were added, the reaction mixture then stirred and heated again to reflux for an additional hour. The reaction mixture was cooled to 45° C. and 12 g (0.1 mole), N-methyldiethanolamine were added while stirring. The reaction exotherm was controlled to a maximum of 70° C. After 10 minutes, the reaction mixture was refluxed for 2 hours to complete the urethane-forming reaction. The resulting adduct was converted to a cationic salt by reacting one half of the reaction product (containing 0.05 mole of the adduct) with 7 g (0.076 mole) epichlorohydrin at 85° C. The reaction mixture became foamy and more viscous as the heating continued. After 2 hours of refluxing, 150 ml of deionized water were added and the ethyl acetate removed by azeotropic distillation. An additional 300 ml water was then added to yield a stable aqueous dispersion containing about 20 percent solids having the formula

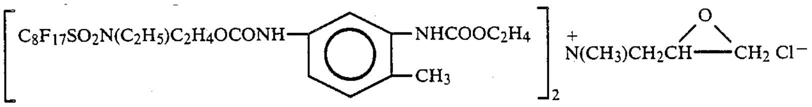

19

EXAMPLES 20, 21

Following the procedure of Example 1, N-methylperfluorooctanesulfonamidoethyl acrylate, hexamethylene diamine, and 1,2-epoxydecane or 1,2-epoxyoctadecane were reacted and the resulting fluorochemical amine adducts were neutralized with glycolic acid to form salts of the formulas

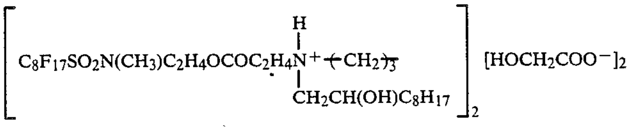

20

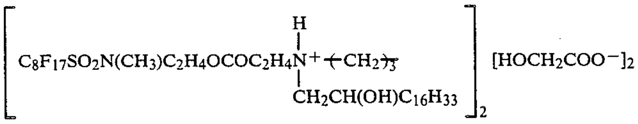

21

EXAMPLE 22

The procedure of Example 1 was followed, using xylylene diamine instead of hexamethylene diamine, to prepare a salt of the formula:

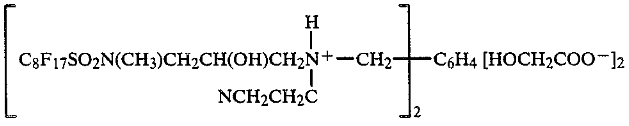

22

EXAMPLE 23

Following the procedure of Example 1, a compound of the formula:

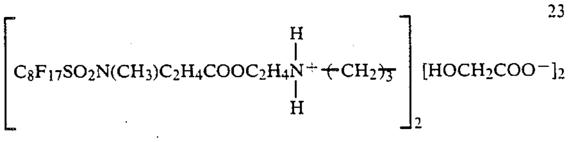

23 was prepared by reacting N-methylperfluorooctanesulfonamidoethyl acrylate and hexamethylene diamine and neutralizing the resulting adduct with glycolic acid.

EXAMPLE 24

The procedure of Example 19 was followed, using diethyl sulfate instead of epichlorohydrin to form a quaternary salt of the formula:

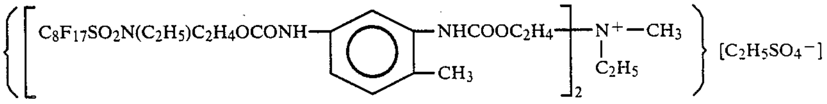

24

EXAMPLE 25

The procedure of Example 1 was followed by reacting N-methylperfluorooctanesulfonamidoethyl acrylate, hexamethylene diamine, and N-methyl-N-(1,2-epoxypropyl)perfluorooctanesulfonamide and neutralizing the resulting adduct with glycolic acid to form a salt of the formula:

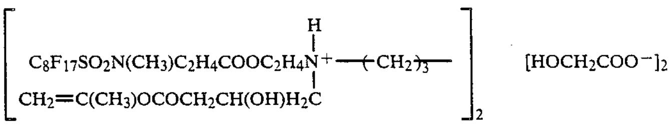

25

EXAMPLE 26

In this example, a number of the fluorochemicals prepared as described above were used in modifying the surface properties of carpet samples during the dyeing thereof in a laboratory dyeing apparatus. The samples of carpet were that of a scoured, greige nylon 6,6 carpet having a pile weight of 26.6 ozs/yd$^2$, 13.1 stitches/inch, and a pile height of 1/4 inch, each sample weighing 25 g.

The laboratory dyeing apparatus was that sold as "AHIBA Turbomat TM6B" (whose construction and operation is described in bulletin A-102-B-DE-1) of Ahiba AG.

The dye bath composition for each of the evaluation runs made was as follows:

TABLE 1

| Ingredient | Amt., ml |
|---|---|
| 1. Deionized water | 750 |
| 2. $Na_2SO_4$ (10% aqueous solution) | 2.5 |
| 3. Dye* (1.9% aqueous solution) | 2.5 |
| 4. Non-ionic leveling agent ("Levegal ANP") (10% aqueous dispersion) | 2.5 |
| 5. Fluorochemical amine salt compound (10% aqueous dispersion) | 2.5 |
| 6. Acetic acid (1% aqueous solution) | 5 |

*A mixture of 3.5 g "Nylosan" Red C-BNL, 4.4 g "Tectilon" Blue 4R-KWL, and 11.0 g "Tectilon" Yellow 913 D In each run, the carpet sample was wrapped around the perforated metal sample holder, secured with rubber bands and placed in a dyeing beaker, and the beaker placed in the bath casing. Then the above-described dye bath composition (except for the acetic acid) were added in the order listed above and the resulting bath contents heated to 96° C. and held at this temperature for 45 minutes, during which time the bath was circulated through the carpet sample by the magnetically driven pump disposed at the lower end of the dyeing beaker. The acetic acid ingredient was added in two increments during the 45 minute period, the first 2.5 ml after 15 minutes and the second 2.5 ml after 30 minutes. The sample holder, with carpet sample still attached thereto was removed from the dye bath after it cooled to about 60° C. and placed in a cooled water rinse bath. The sample was then removed from the holder and centrifuged to remove most of the water. The carpet sample was then dried in air at 70° C. for 10 min. The dried carpet samples were then evaluated for water and oil repellency.

The water repellency test is one which often is used for this purpose. The aqueous stain or water repellency of treated samples is measured using a water/isopropyl alcohol test, and is expressed in terms of a water repellency rating of the treated carpet or fabric. Treated carpets which are penetrated by or resistant only to a 100 percent water/0 percent isopropyl alcohol mixture, the least penetrating of the test mixtures, are given a rating of 100/0, whereas treated fabrics resistant to a 0 percent water/100 percent isopropyl alcohol mixture, the most penetrating of the test mixtures, are given a rating of 0/100. Other intermediate values are determined by use of other water/isopropyl alcohol mixtures, in which the percentage amounts of water and isopropyl alcohol are each multiples of 10. The water repellency rating corresponds to the most penetrating mixture which does not penetrate or wet the fabric after 15 seconds contact. In general a water repellency rating of 90/10 or better is desirable.

The oil repellency test is also one which is often used for this purpose. The oil repellency of treated carpet and textile samples is measured by AATCC Standard Test 118—1978, which test is based on the resistance of treated fabric to penetration by oils of varying surface tensions. Treated fabrics resistant only to "Nujol", a brand of mineral oil, and the least penetrating of the test oils, are given a rating of 1, whereas treated fabrics resistant to heptane, the most penetrating of the test oils, are given a value of 8. Other intermediate values are determined by use of other pure oils or mixtures of oils. The rated oil repellency corresponds to the most penetrating oil (or mixture of oils) which does not penetrate or wet the fabric after 30 seconds contact. Higher numbers indicate better oil repellency. In general, an oil repellency of 2 or greater is desirable.

The following table summarizes the results obtained by treating carpet samples with various fluorochemicals during the dyeing of the carpet samples, as described above.

TABLE 2

| Formula of Fluorochemical Used | Properties of Treated Carpet Samples: Oil Repellency | Properties of Treated Carpet Samples: Water Repellency |
|---|---|---|
| 1 | 5 | 70/30 |
| 2 | 4 | 80/20 |
| 3 | 5 | 70/30 |
| 4 | 5 | 70/30 |
| 5 | 5 | 70/30 |
| 6 | 2 | 90/10 |
| 7 | 3 | 80/20 |
| 8 | 5 | 80/20 |
| 9 | 4 | 80/20 |
| 10 | 4 | 80/20 |
| 11 | 3 | 80/20 |
| 12 | 3 | 80/20 |
| 13 | 5 | 80/20 |
| 14 | 0 | 90/10 |
| 15 | 3 | 90/10 |
| 16 | 1 | 90/10 |
| 17 | 3 | 90/10 |
| 18 | 0 | 90/10 |
| 20 | 2 | 70/30 |
| 21 | 1 | 70/30 |

As shown in Table 2, most of the fluorochemical compounds of this invention imparted desirable repellency properties to the carpet samples. Although in a few runs where marginal properties were achieved (with a 70° C. drying temperature), improved results were obtained in duplicate runs where the treated carpet was dried at the higher temperature of 130° C. For example, fluorochemical of formula 6 resulted in an oil repellency of 4 and a water repellency of 70/30 when the carpet was dried instead at 130° C. for 10 min. As for the fluorochemicals 14 and 18 although they did not impart the degree of oil repellency desired, see Table 5, Runs 5 and 6, where they did impart desired results in a different mode of application.

EXAMPLE 27

In a number of runs, the procedure of Example 26 was followed, except that instead of adding fluorochemical to the dye bath, the fluorochemical (formula 1) was added to the water rinse bath to provide it in the amount of 1800 ppm, together with a salt added to the rinse bath to aid exhaustion of the fluorochemical. The water rinse bath had a pH of about 4 to 5. A summary of the runs is shown in the following Table.

TABLE 3

| Run | Salt Exhaustion Aid | Oil Repellency | Water Repellency |
|---|---|---|---|
| 1 | $Na_2SO_4$ | 5 | 70/30 |
| 2 | $MgCl_2$ | 2 | 80/20 |
| 3 | $(NH_4)_2SO_4$ | 5 | 70/30 |
| 4 | $(Al)_2(SO_4)_3$ | 4 | 70/30 |
| 5 | Sodium citrate | 5 | 70/30 |
| 6 | $CaCl_2$ | 2 | 80/20 |
| 7 | $NH_4Cl$ | 2 | 80/20 |
| 8 | KCl | 2 | 70/30 |
| 9 | none | 0 | 80/20 |

EXAMPLE 28

A number of fluorochemical treating agents of this invention, whose preparations are described herein above, were used to treat carpet samples, using for this purpose a laboratory dyeing machine sold under the trademark Launder-Ometer, Model LEF, as described in Bulletin No. 1295 B, of the Atlas Electric Devices Company. The carpet used was a nylon 6,6 which was the same as in the previously described examples. The bath used in applying the fluorochemical had the following composition.

TABLE 4

| Treating Bath Ingredient | Amt., ml |
|---|---|
| 1. Deionized water | 800 |
| 2. $(NH_4)_2SO_4$ buffer (5% aqueous) | 4 |
| 3. Fluorochemical (20% aqueous dispersion) | 0.3 |
| 4. Non-ionic leveling agent ("Tridye", 10% aqueous solution) | 2 |

In each run, the carpet sample was placed in a steel specimen container, which was then mounted on a rotor adapted to be rotated in a constant temperature water bath. The loaded specimen container is heated to 96° C. and rotated for 45 minutes, cooled to about 30° C., and the treated carpet samples are then removed from the container, rinsed, centrifuged to remove excess water, and dried for 30 minutes at 70° C. The oil repellency and water repellency of the dried samples were then tested by the procedure described herein above. In addition, the amount of fluorochemical deposited on the carpet samples was found by determining the amount of elemental fluorine in order to thereby find the degree of exhaustion or deposition of the fluorochemical from the treating bath. Results are summarized in the following table.

TABLE 5

| Run | Formula of Fluoro-chemical Used | Oil Repel-lency | Water Repel-lency | Amt. Fluorine Deposited, ppm | Degree of Fluoro-chemical Exhausted, % (approx.) |
|---|---|---|---|---|---|
| 1 | 1A | 0 | 100/0 | 360 | 60 |
| 2 | 1 | 5 | 70/30 | 750 | 100 |
| 3 | 13A | 0 | 80/20 | 540 | 90 |
| 4 | 13 | 2 | 80/20 | 630 | 100 |
| 5 | 14 | 5 | 70/30 | 450 | 75 |
| 6 | 18 | 3 | 90/10 | 320 | 50 |
| 7 | 22 | 4 | 80/20 | 420 | 70 |
| 8 | 23 | 5 | 70/30 | 400 | 67 |
| 9 | 19 | 5 | 70/30 | 540 | 90 |
| 10 | 24 | 3 | 70/30 | 450 | 75 |
| 11 | 25 | 5 | 90/10 | 400 | 67 |

The above table shows in Runs 1-4 that when the fluorochemical is in the form of its salt form formulas 1 and 13, the oil repellency of the carpet treated therewith is significantly greater, and the water repellency of the treated carpet is also better or equivalent, to those results obtained when the fluorochemical was in its free amine form, formulas 1A and 13A.

The above data also show that approximately 100 percent of the fluorochemical in the treating bath is exhausted in the case where such adduct is used, viz., the fluorochemicals of formulas 1 and 13.

EXAMPLE 29

An Aqueous dispersion of 0.4 wt. % of the fluorochemical treating agent of formula 1 was applied as a primary spin finish (together with a coconut-based lubricant) to freshly extruded, undrawn yarn of nylon 6 fibers. The yarn was made up of 118 filaments of 18 denier and the fluorochemical was applied using a commercial spin finish applicator. The thus treated yarn was continuously drawn and texturized, and then made into level-loop carpet (28 oz/yd$^2$), heat set at 196° C. for one minute, acid dyed, dried, and then evaluated for oil and water repellency. The water repellency was 70/30 and the oil repellency was 4, using the test procedure herein above described. The treated sample was also analyzed to determine the amount of fluorochemical deposited and it was found that it contained 320 ppm fluorine, since the corresponding amount of fluorine deposited on the fiber before dyeing was 470 ppm, the amount of fluorochemical retained after dyeing was about 70 percent. The soil resistance of the carpet was also evaluated by a "Walk-On Test" often used in the carpet industry, viz., AATCC Test Method 122-1976. This is a comparative test in which a treated and untreated (control) sample are placed side-by-side in a heavily travelled industrial area for an exposure of about 7,000 steps. The samples are rotated periodically to insure uniform exposure and are vaccumed every 24 hours during the test and before visual evaluation. Using this test, the treated carpet was found to have a significant improvement in soil resistance when compared to the untreated sample.

EXAMPLE 30

A loosely knitted fabric of carrierless polyester carpet yarn (12 denier per filament), was treated with an aqueous dispersion of 0.18 wt. % of the fluorochemical of formula 1 by a padding operation. The treated fabric was dried for 15 minutes at 160° C., disperse dyed, using the apparatus of Example 28, and dried. The treated fabric was found to have an oil repellency of 5 and a water repellency value of 80/20. The dyed carpet was found to have 390 ppm fluorine (as compared to 614 ppm fluorine before dyeing), thus 64 percent of the fluorochemical treating agent deposited was retained after dyeing.

EXAMPLE 31

Nylon taffeta apparel fabric (light weight, single ply, uncoated) was sprayed with an aqueous dispersion of 0.42 wt. % fluorochemical treating agent of formula 1. Wet pick up was at the 25 percent level, thus depositing 0.1 wt. % fluorochemical solid on the fabric. The treated fabric was then dried for 10 minutes at 150° C., and the oil repellency was determined by the test herein above described. The water spray rating of the treated fabric was also evaluated.

The water spray rating is measured by Standard Test Number 22, published in the 1977 Technical Manual and Yearbook of the American Association of Textile Chemists and Colorists (AATCC). The spray rating is measured using a 0 to 100 scale where 100 is the highest possible rating. In general, a spray rating of 70 or greater is desirable, particularly for outerwear fabrics.

In a similar top spray application, the fluorochemical treating agent was applied to an apparel fabric made of woven polyester (style Seville/Suraline), and an apparel fabric made of polyester double knit (style 1418), the amounts deposited on these fabrics being 0.3 wt. % and 0.4 wt. %, respectively. Results are shown in the following table.

TABLE 6

| Fabric | Oil Repellency | Water Spray Rating |
|---|---|---|
| Nylon (taffeta) | 6 | 50 |
| Polyester (woven) | 5 | 70 |
| Polyester (double knit) | 6 | 70 |

EXAMPLE 32

A sample of chrome-tanned leather was treated with an aqueous dispersion of 0.67 wt. % of the fluorochemical of formula 1 in a drumming operation. The amount of fluorochemical deposited on the leather was 2 wt. %. The treated leather was dried in air. The grain and suede sides of the treated leather were found to have oil repellency values of 4 and 6 respectively and the water repellency values for the grain and suede sides were found to be 80/20 on both sides. (Untreated chrome-tanned leather has essentially no oil or water repellency.)

Similarly, a sample of chrome-tanned, dyed, fat liquored leather was treated with the fluorochemical of formula 1 and was found to have oil repellency values of 2 and 5 on the grain and suede side, respectively, and a water repellency value of 70/30 for the suede side.

EXAMPLE 33

The fluorochemicals of formulas 1 and 19 were applied as an aqueous dispersion to a sheet of water-leaf paper using a laboratory press yielding 145 percent wet pick up. The results of three such runs are summarized in the following table.

TABLE 7

| Run | Formula of Fluoro-chemical Used | Conc. of Fluoro-chemical in Bath, wt. % | Amount of Fluoro-chemical on Paper wt. % | Oil Repel-lency* | Water Repel-lency** |
|---|---|---|---|---|---|
| 1 | 1 | 0.07 | 0.1 | 7 | No water repellency |
| 2 | 1 | 0.14 | 0.2 | 7 | No water repellency |
| 3 | 1 | 0.21 | 0.3 | 8 | 75 |
| 4 | 19 | 0.07 | 0.1 | 4.5 | 88 |
| 5 | 19 | 0.14 | 0.2 | 6.5 | 41 |
| 6 | 19 | 0.21 | 0.3 | 7 | 30 |

*This was determined by the "Kit Test" described as TAPPI Useful Method 557; the higher the value, the better the oil repellency.
**This was determined by the "Cobb Test" described as TAPPI-T441-os-77; the lower the value, the better the water repellency.

The data in the above table show that for some fluorochemicals of this invention, large amounts of them may have to be deposited on the paper to obtained desired water repellency. However, such fluorochemical can be used in an amount sufficient to obtain the desired degree of oil repellency and they can be used in conjunction with hydrocarbon treating agents, e.g. ketene dimers, commonly used to impart water repellency to paper.

Various modifications and alterations of this invention will be apparent to those skilled in the art without departing from the scope and spirit of this invention.

I claim:

1. Compounds of the formula

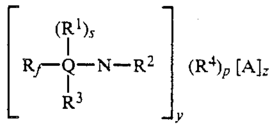

where $R_f$ is a fluorinated, saturated, monovalent, aliphatic, stable, non-polar, inert, oleophobic, hydrophobic radical having 3 to 20 carbon atoms and 40 to 78 weight percent fluorine and terminating in at least three fully fluorinated carbon atoms;

Q is an organic linking group which is one or a combination of polyvalent aliphatic groups, polyvalent aromatic groups, oxy (—O—), thio (—S—), carbonyl (—CO—), sulfonamido $(-SO_2N-)$, carbonamido (—CON—), hydroxymethylene (—CH(OH)—), carbamato (—NHCOO—) and urylene (—NHCONH) organic linking moieties, with the proviso that the moiety of Q which is bonded to the nitrogen atom of the amine salt group is not an electrophilic moiety and that Q is bonded to the nitrogen atom of the amine salt group by a methylene moiety;

N is a tertiary amino nitrogen atom or quaternary amino nitrogen atom;

$R^1$ is a hydrogen or an alkyl group, $R^2$ is $R_fQ$—, alkyl groups, alkyl groups containing an —O— hetero atom, alkyl groups containing an —S— hetero atom, alkyl groups containing an

—N— hetero atom, aryl groups, aryl groups containing an —O— hetero atom, aryl groups containing an —S— hetero atom, aryl groups containing an

—N— hetero atom, combinations of such groups, alkylene groups, arylene groups or combinations of arylene and alkylene groups;

$R^3$ is a cyanoalkyl moiety;

$R^4$ is an alkylene or arylene group;

A is an anion derived from a protonic acid or an alkylating agent;

s is 1;

y is 1 to 4;

p is 0 to 1;

z is 1 to 4;

with the provisos that (1) when y is 1, then p is 0 and z is 1, and (2) when y is 2, then $R^2$ is said alkylene or arylene group or combination thereof, and said compounds contain at least about 20 weight-percent carbon-bonded fluorine the locus of which is in said $R_f$ radical.

2. Compounds of the formula

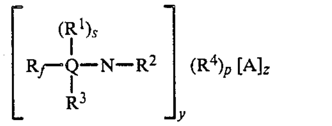

where $R_f$ is a stable, inert, non-polar, fluoroalkyl radical having 3 to 20 carbon atoms, 40 to 78 weight-percent fluorine, and a terminal portion having at least three fully fluorinated carbon atoms, said fluoroalkyl radical being selected from straight chain radicals, branched chain radicals, cyclic radicals, and combinations thereof;

Q is an organic linking group which is one or a combination of polyvalent aliphatic groups, polyvalent aromatic groups, oxy (—O—), thio (—S—), carbonyl (—CO—), sulfonamido

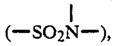

carbonamido

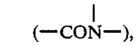

hydroxymethylene (—CH(OH)—), carbamato (—NHCOO—) and urylene (—NHCONH) organic linking moieties, with the proviso that the moiety of Q which is bonded to the nitrogen atom of the amine salt group is not an electrophilic moiety and that Q is bonded to the nitrogen atom of the amine salt group by a methylene moiety;

N is a tertiary amino nitrogen atom or quaternary amino nitrogen atom;

$R^1$ is a hydrogen or an alkyl group, $R^2$ is $R_fQ$—, alkyl groups, alkyl groups containing an —O— hetero atom, alkyl groups containing an —S— hetero atom, alkyl groups containing an

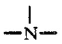

hetero atom, aryl groups, aryl groups containing an —O— hetero atom, aryl groups containing an —S— hetero atom, aryl groups containing an

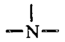

hetero atom, combinations of such groups, alkylene groups, arylene groups or combinations of arylene and alkylene groups;

$R^3$ is $CH_2CH_2CN$;

$R^4$ is an alkylene or arylene group;

A is an anion derived from a protonic acid or an alkylating agent;

s is 1;

y is 1 to 4;

p is 0 to 2;

z is 1 to 2;

with the provisos that (1) when y is 1, then p is 0 and z is 1, and (2) when y is 2, then $R^2$ is said alkylene or arylene group or combination thereof, and said compounds contain at least about 20 weight-percent carbon-bonded fluorine the locus of which is in said $R_f$ radical.

3. Compounds of the formula

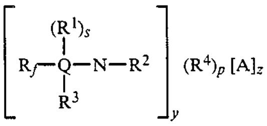

where $R_f$ is $C_nF_{2n+1}$- wherein n is 3 to 20;

Q is an organic linking group which is one or a combination of polyvalent aliphatic groups, polyvalent aromatic groups, oxy (—O—), thio (—S—), carbonyl (—CO—), sulfonamido

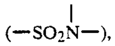

carbonamido

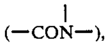

hydroxymethylene (—CH(OH)—), carbamato (—NHCOO—) and urylene (—NHCONH—) organic linking moieties, with the proviso that the moiety of Q which is bonded to the nitrogen atom of the amine salt group is not an electrophilic moiety and that Q is bonded to the nitrogen atom of the amine salt group by a methylene moiety;

N is a tertiary amino nitrogen atom or quaternary amino nitrogen atom;

$R^1$ is a hydrogen or an alkyl group, $R^2$ is alkyl groups, alkyl groups containing an —O— hetero atom, alkyl groups containing an —S— hetero atom, alkyl groups containing an

hetero atom, aryl groups, aryl groups containing an —O— hetero atom, aryl groups containing an —S— hetero atom, aryl groups containing an $$-\overset{|}{N}-$$

hetero atom, combinations of such groups, alkylene groups, arylene groups or combinations of arylene and alkylene groups;

$R^3$ is $CH_2CH_2CN$;

$R^4$ is an alkylene or arylene group;

A is an anion derived from a protonic acid or an alkylating agent;

s is 1;

y is 1 to 4;

p is 0 to 2;

z is 1 to 2;

with the provisos that (1) when y is 1, then p is 0 and z is 1, and (2) when y is 2, then $R_2$ is said alkylene or arylene group or combination thereof, and said compounds contain at least about 20 weight-percent carbon-bonded fluorine the locus of which is in said $R_f$ radical.

4. A compound of the formula $$\left[C_8F_{17}SO_2N(CH_3)CH_2CH(OH)CH_2\overset{\overset{H}{|}}{\underset{\underset{CH_2CH_2CN}{|}}{N^+}}\!\!-\!\!(CH_2)_3\right]_2 [HOCH_2COO^-]_2$$

5. A compound according to claim 1 wherein said cyanoalkyl moiety is $CH_2CH_2CN$.

6. The compounds of claim 1 wherein said $R_f$ is selected from straight chain radicals, branched chain radicals, cyclic radicals, and combinations thereof, which radicals can contain hetero atoms selected from catenary oxygen and trivalent nitrogen atoms bonded only to carbon atoms.

* * * * *